(12) United States Patent
Peng et al.

(10) Patent No.: US 8,889,887 B2
(45) Date of Patent: Nov. 18, 2014

(54) PENTAMETHINE CYANINE FLUORESCENT DYES, PREPARATION METHODS AND USES THEREOF

(75) Inventors: Xiaojun Peng, Liaoning (CN); Zhigang Yang, Liaoning (CN); Yanxia He, Liaoning (CN); Jingyun Wang, Liaoning (CN); Jiangli Fan, Liaoning (CN); Shiguo Sun, Liaoning (CN); Fengling Song, Liaoning (CN)

(73) Assignees: Dalian University of Technology, Dalian (CN); Dalian Firstar Information Materials Co., Ltd., Dalian (CN)

( * ) Notice: Subject to any disclaimer, the term of this patent is extended or adjusted under 35 U.S.C. 154(b) by 0 days.

(21) Appl. No.: 13/982,089

(22) PCT Filed: Jan. 31, 2011

(86) PCT No.: PCT/CN2011/170841
§ 371 (c)(1),
(2), (4) Date: Jul. 26, 2013

(87) PCT Pub. No.: WO2012/103678
PCT Pub. Date: Aug. 9, 2012

(65) Prior Publication Data
US 2013/0309715 A1 Nov. 21, 2013

(51) Int. Cl.
C07D 403/06 (2006.01)
G01N 33/52 (2006.01)
C09B 23/01 (2006.01)

(52) U.S. Cl.
CPC .............. G01N 33/52 (2013.01); C07D 403/06 (2013.01); C09B 23/005 (2013.01); C09B 23/0058 (2013.01); C09B 23/0008 (2013.01)
USPC ...................................................... 548/455

(58) Field of Classification Search
USPC ...................................................... 582/455
See application file for complete search history.

(56) References Cited

U.S. PATENT DOCUMENTS

| 5,453,505 A | 9/1995 | Lee et al. |
| 6,114,350 A | 9/2000 | Randall et al. |

FOREIGN PATENT DOCUMENTS

| CN | 101787218 A | 7/2010 |
| JP | 2000-159774 A | 6/2000 |
| WO | 2009/121055 A1 | 10/2009 |

OTHER PUBLICATIONS

Wang Li, et al, "Novel Asymmetric Cy5 Dyes: Synthesis, Photostabilities and High Sensitivity in Protein Fluorescence Labeling", Journal of Photochemistry and Photobiology A: Chemistry 210 (2010), pp. 168-172. Elsevier, Amsterdam.

*Primary Examiner* — Shawquia Jackson
(74) *Attorney, Agent, or Firm* — Novick, Kim & Lee, PLLC; Allen Xue (57) ABSTRACT

A pentamethine cyanine fluorescent dye having the general formula I, a synthetic method and a use thereof are disclosed. In the general formula, X is CHO or $CHCR_3R_4$; $R_1$ and $R_2$ are independently selected from the group consisting of $(CH_2)_n R_7$ and et al.; $R_3$ and $R_4$ are independently selected from the group consisting of CN, COOH and $COOR_{16}$; $R_5$, $R_6$ and $R_7$ are independently selected from the group consisting of H, $SO_3R_{10}$ and $COOR_{11}$; $R_8$ is H or $C_{1-18}$ alkyl; $R_9$ is H or $CH_3$; $R_{10}$ is $N(R_{12}R_{13}R_{14}R_{15})$; $R_{11}$ is $C_{1-18}$ alkyl; $R_{12}$, $R_{13}$, $R_{14}$, $R_{15}$ and $R_{16}$ are independently selected from the group consisting of H, $C_{1-18}$ alkyl, $(CH_2)_m OR_8$ and $(CHR_9CH_2O)_p R_8$; $Y^-$ is halogen anion or $OTs^-$; and n, m and p are integers of 0-18. The dye can be utilized to sensitively detect viscosity of micro-environment such as tissues and cells.

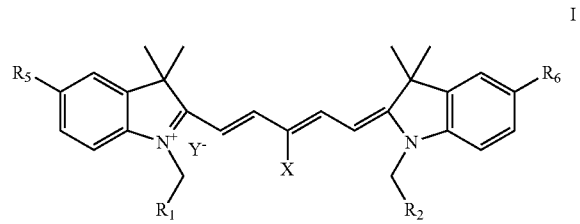

10 Claims, 6 Drawing Sheets

PENTAMETHINE CYANINE FLUORESCENT DYES, PREPARATION METHODS AND USES THEREOF

TECHNICAL FIELD OF THE INVENTION

The present invention relates to a pentamethine cyanine fluorescent dye, especially a novel fluorescent dye with a substituent group conjugated at central position of the pentamethine chain, a synthetic method thereof, and a method of utilizing the fluorescent dye as a viscosity-sensitive fluorescent probe to detect viscosity of micro-environment in live cells.

BACKGROUND OF THE INVENTION

Viscosity is an important factor to evaluate fluidity and diffusion of a condensed fluid, and is an important reference index of fluid diffusion rate as well. For a condensed fluid with macroscopically large volume, the methods and the devices such as rotational viscometer and falling ball viscometer for detecting fluid viscosity have been well developed, however these viscometers can only be used to detect fluid viscosity of macroscopically large volume, and at least 1 mL of fluid volume is needed. For viscosity detection of micro-environment at tissue level or cell level, these detection methods and devices generally can not be used. It is very meaningful to accurately detect viscosity of micro-environment at cell level, since viscosity is different in different position of a live cell, and cellular viscosity strongly influences diffusion and transportation of biomolecules and signals in cells. According to the work of K. Suhling and his coworkers, viscosity in membrane system micro-environment can reach up to 140 centipoise (cp) in a normal live cell, but viscosity in cytoplasm is merely 1-2 cp which is equivalent to that of water; intracellular viscosity is evidently increased when pathological changes happen in a cell and the cell becomes dead, and the highest viscosity can reach up to 300 cp, the obvious viscosity change in a cell would result in diseases or dysfunctions of organ and body. Therefore, it is necessary to develop a method to detect viscosity of micro-environment.

Recently, a method of utilizing a viscosity probe based on a fluorescent molecule rotor to detect viscosity of micro-environment in a cell was reported. The basic rationale for the viscosity probe involves fluorescence lifetime imaging and fluorescence ratiometry imaging. For the fluorescence lifetime imaging, much excellent work has been done. Emission wavelength of the fluorescence lifetime imaging only has a single emission peak, according to the work of A. Theodorakis and his coworkers, there are two methods for designing double-wavelength viscosity molecule rotor, one of which is a method based on photo-induced intramolecular charge transfer (ICT), but the probe designed according to the mechanism is easily influenced by solvent polarity; another method is to design molecule rotor based on fluorescence resonance energy transfer, but the method needs a good spectral overlap between emission spectra of energy donor and absorption spectra of energy receptor; furthermore, the various molecular orientations of the dipolar moments between the energy transfer pairs probably increase the uncertainties of final results, which inhibits the further design and application of the probe.

Precision and reliability are very important for cell imaging. Although Suhling etc. and Theodorakis's group developed fluorescence lifetime imaging and fluorescence ratiometry imaging to detect viscosity change, respectively. However, at present no fluorescence probe can be employed to evaluate viscosity by both methods at the same time.

Traditional pentamethine cyanine fluorescent dyes are synthesized by the reaction of a quaternary salt and a condensing reagent having a conjugated chain, with anhydrous sodium acetate as a catalyst in acetic anhydride solvent under argon atmosphere. Generally, pentamethine cyanine fluorescent dyes have advantages over the other fluorephores, e.g. large molar extinction coefficient (up to $10^5$ level), near infrared absorption and emission and suitable fluorescence quantum yields etc., so they have been widely applied in protein labeling, DNA sequence analysis, ion and neutral small molecule recognition, and bioimaging in vitro and in vivo. However, up to now, it has not been reported that pentamethine cyanine dyes could be designed as molecular rotors sensitive to environment viscosity for detecting viscosity of solution or intracellular environment.

SUMMARY OF THE INVENTION

The present invention aims to provide a novel pentamethine cyanine fluorescent dye which is very sensitive to environmental viscosity, its fluorescence property is little influenced by solvent polarity, and has double functions in detection of environmental viscosity to guarantee its usability in both fluorescence lifetime imaging and fluorescence ratiometry imaging. The present inventors found that, when a substituent group was conjugated to central position of the pentamethine chain of traditional pentamethine cyanine fluorescent dyes, spectra of the dyes exhibited two absorption and emission peaks. Because of rotation of the substituent group it is easy to form TICT exited state to consume most of the excited energy, resulting in getting back of the dye to ground state mainly by non-radiation. The compounds are capable of avoiding the influence of solvent polarity, and are very sensitive to environmental viscosity. With the increase of environmental viscosity, the rotation of the substituent group of the dye is inhibited, and fluorescence intensities at two emission peaks are increased in different scales showing ratiometric change; simultaneously fluorescence lifetimes are elongated along with the increase of viscosity. Both changes are tightly related to viscosity variation. Therefore, the compound can be used for cellular viscosity imaging in different regions or viscosity changes, which may provide a promising viscosity detecting tool in biological application.

Therefore, firstly, the present invention provides a pentamethine cyanine fluorescent dye having the following general formula I:

wherein,

X is CHO or $CHCR_3R_4$;

$R_1$ and $R_2$ are independently selected from the group consisting of $(CH_2)_nR_7$, $(CH_2)_mOR_8$, $(CHR_9CH_2O)_pR_8$ and $CH_2C_6H_4R_7$;

$R_3$ and $R_4$ are independently selected from the group consisting of CN, COOH and $COOR_{16}$;

$R_5$, $R_6$ and $R_7$ are independently selected from the group consisting of H, $SO_3R_{10}$ and $COOR_{11}$;

$R_8$ is H or $C_{1-18}$ alkyl;

$R_9$ is H or $CH_3$;

$R_{10}$ is $N(R_{12}R_{13}R_{14}R_{15})$;

$R_{11}$ is $C_{1-18}$ alkyl;

$R_{12}$, $R_{13}$, $R_{14}$, $R_{15}$ and $R_{16}$ are independently selected from the group consisting of H, $C_{1-18}$ alkyl, $(CH_2)_mOR_8$ and $(CHR_9CH_2O)_pR_8$;

$Y^-$ is halogen anion or $OTs^-$; and n, m and p are integers of 0-18.

The term of "alkyl" in the present invention includes linear and branched alkyl; the term of "halogen" includes fluorine, chlorine, bromine and iodine; and OTs- is p-toluenesulfonate ion.

Among the compounds of the present invention, the compound in which $R_3$ and $R_4$ are CN, namely the compound in which substituent group X is aldehyde group or malononitrile vinyl group, is preferable.

The substituent group in the matirc structure of the compounds of the present invention has a function of adjusting solubility of the dye in organic or aqueous solution, or transmembrane ability. Preferably, $R_1$ and $R_2$ are independently selected from $(CH_2)_nR_7$ and/or both $R_5$ and $R_6$ are H.

Most preferably, $R_3$ and $R_4$ are CN, $R_1$ and $R_2$ are $CH_3$, $R_5$ and $R_6$ are H, namely the compound of formula 4 and the compound of formula 7 are most preferable.

4

7

Another aim of the present invention is to provide a synthetic method of the above-mentioned compound, consisting of the following steps:

(1) 2,3,3-trimethyl-3H-indole with a substituent group of $R_5$ is reacted with $R_1CH_2Z$ to obtain a quaternary ammonium salt II, wherein Z is halogen or OTs, $Z^-$ is halogen anion or $OTs^-$, reaction temperature is 80-148° C., reaction time is 6-12 hours, reaction solvent is selected from the group consisting of toluene, ortho-dichlorobenzene, ethanol and acetonitrile, and molar ratio of the indole to $R_1CH_2Z$ is 1:1-1:4;

II

In the step, a small amount of KI can be added into reaction system as a catalyst when Z is chlorine or bromine, which can accelerate reaction speed and reduce reaction time.

(2) 2-bromoacetic acid is reacted with $POCl_3$ and DMF to obtain an intermediate III with multi aldehyde groups, wherein molar ratio of 2-bromoacetic acid to $POCl_3$ is 1:4-1:6, and reaction temperature is 70±2° C.;

III

In this step, it is unnecessary to limit the ratio of DMF to 2-bromoacetic acid because DMF is used as solvent.

(3) the quaternary ammonium salt II obtained in the step (1) and the intermediate III obtained in the step (2) are refluxed for 2-6 hours in ethanol solvent with pyridine as a catalyst to obtain a pentamethine cyanine fluorescent dye of formula IV with aldehyde group at central position, wherein when molar ratio of the intermediate III to the quaternary ammonium salt II is 1:3, the product is a symmetrical pentamethine cyanine fluorescent dye with aldehyde group at the central position, while when two kinds of the quaternary ammonium salts are used, and molar ratio of the intermediate III, the first quaternary ammonium salt and the second quaternary ammonium salt is 1:0.8-1:1-3, the product is an asymmetrical pentamethine cyanine fluorescent dye with aldehyde group at the central position;

IV (4) the compound IV obtained in the step (3) is reacted with $NaBH_4$ in methanol to obtain a compound V;

V

In this step, the added amount of $NaBH_4$ should be as small as possible. To avoid reducing aldehyde group at the central position, it is better that the added amount of NaBH$_4$ is the amount of just reducing positive charge of the dye. The addition of NaBH$_4$ can be controlled sensitively by the color change in the reaction solution, NaBH$_4$ is slowly added into the compound solution with deep blue color under stirring until the blue color of solution exactly disappears and turns to yellow color.

(5) the compound V obtained in the step (4) is reacted with R$_3$CH$_2$R$_4$ under basic condition to obtain a compound VI, wherein reaction solvent is anhydrous methanol, reaction temperature is 25-40° C., and molar ratio of the compound V to R$_3$CH$_2$R$_4$ is 1:2-1:4;

VI (6) the compound VI obtained in the step (5) is oxidized and dehydrogenated to obtain a compound VII, wherein solvent is dichloromethane or chloroform, oxidation-dehydrogenation reagent is 2,3,5,6-tetrachloro-1,4-p-benzoquionone or 2,3-dichloro-5,6-dicyano-1,4-p-benzoquionone, and molar ratio of the compound V to the oxidation-dehydrogenation reagent is 1:0.5-1:1;

VII (7) ion exchange is performed between the compound IV and the compound VII with a sodium salt or a potassium salt containing Y$^-$ anion to obtain the compound of formula I.

Another aim of the present invention is to provide a method of utilizing the pentamethine cyanine fluorescent dye to detect fluid viscosity, especially fluid viscosity at tissue level and cell level.

The pentamethine cyanine dye substituted at central position disclosed in the present invention has dual absorption and emission peaks, and its fluorescence is very sensitive to the viscosity of solvent. The fluorescence intensity of the dye increases with the increase of the viscosity of solvent, which is well fit for Förster-Hoffmann equation. Moreover, the logarithm of ratio value of fluorescence intensity at each emission peak as well as the logarithm of fluorescence lifetime keeps linear relationship with the logarithm of viscosity, which is also fit for Förster-Hoffmann equation, so the viscosity in solution or biological environment can be detected by the above two methods. The dye can be employed to study cells by fluorescence ratiometry imaging and fluorescence lifetime imaging and to detect the change of intracellular viscosity by fluorescence ratiometry imaging as well.

BRIEF DESCRIPTION OF DRAWINGS

There are 11 figures included in the present invention.

FIG. 1A. Absorption spectra of the compound 4 in different solvents: (1) methylene chloride; (2) acetonitrile; (3) DMSO; (4) ethanol; (5) methanol; (6) water.

FIG. 1B. Emission spectra of the compound 4 in different solvents: (1) methylene chloride; (2) acetonitrile; (3) DMSO; (4) ethanol; (5) methanol; (6) water.

FIG. 4A. Changes of absorption spectra of the compound 7 (1 μM) in solutions with different viscosity.

FIG. 4B. Changes of emission spectra of the compound 7 (1 μM) in solutions with different viscosity ($\lambda_{ex}$=510 nm).

FIG. 4C. Linear relationship between the log($I_{665}/I_{565}$) of 7 (1 μM) vs. log(viscosity).

FIG. 5A. Fluorescence lifetime plot of 7 (1 μM) in mixed solutions with different volume proportion (viscosity) of glycerol and ethanol, excited at 460 nm and detected at 665 nm.

FIG. 5B. Linear relationship of log(τ) and log(viscosity) of 7, fluorescence lifetime equipment version: Horiba Jobin Yvon Fluoromax-4-p.

FIG. 6A. Fluorescence image of blue channel.

FIG. 6B. Fluorescence image of red channel.

FIG. 6C. Merged image by red and blue channels.

FIG. 6D. Fluorescence ratio image of FIG. 4B and FIG. 4A.

FIG. 7A. Fluorescence lifetime plot of 4 (1 μM) in mixed solutions with different proportion of glycerol and ethanol, excited at 376 nm and detected at 650 nm.

FIG. 7B. Linear relationship of log(τ) vs. log(viscosity) of 4.

FIG. 8A. Fluorescence intensity imaging of 4 in MCF-7 cells.

FIG. 8B. Fluorescence lifetime imaging of 4 in MCF-7 cells, excited at 800 nm.

FIG. 9A. The compound 7 (5 μM) was incubated with MCF-7 cells for 30 minutes.

FIG. 9B. MCF-7 cells were firstly treated with $H_2O_2$ (1 mM) for 30 minutes to induce apoptosis, then washed with PBS buffer, and incubated with 7 (5 M) for 30 minutes.

FIG. 9C. MCF-7 cells were firstly incubated with ethanol for 30 minutes to be fixed, then washed with PBS buffer, and incubated with 7 (5 M) for 30 minutes.

FIG. 9D. The dye 7 (5 μM) was incubated with MCF-7 cells for 30 minutes, and then stood at room temperature for 4 hours.

FIG. 10A. The dye 7 (5 μM) was incubated with MCF-7 cells for 30 minutes (fluorescence image of green channel; fluorescence image of red channel, image under white light and merged image by the three images).

FIG. 10B. MCF-7 cells were firstly treated with $H_2O_2$ (1 mM) for 30 minutes to induce apoptosis, then washed with PBS buffer, and incubated with 7 (5 M) for 30 minutes (fluorescence image of green channel; fluorescence image of red channel, image under white light and merged image by the three images).

FIG. 10C. MCF-7 cells were firstly incubated with ethanol for 30 minutes to be fixed, then washed with PBS buffer, and incubated with 7 (5 M) for 30 minutes (fluorescence image of green channel; fluorescence image of red channel, image under white light and merged image by the three images).

FIG. 10D. The compound 7 (5 M) was incubated with MCF-7 cells for 30 minutes, and then stood at room temperature for 4 hours (fluorescence image of green channel; fluorescence image of red channel, image under white light and merged image by the three images).

DETAILED DESCRIPTION OF PREFERRED EMBODIMENTS

The following examples can make the person skill in the art understood the present invention clearly, but do not restrict the present invention in any form.

Example 1

Figure 11:
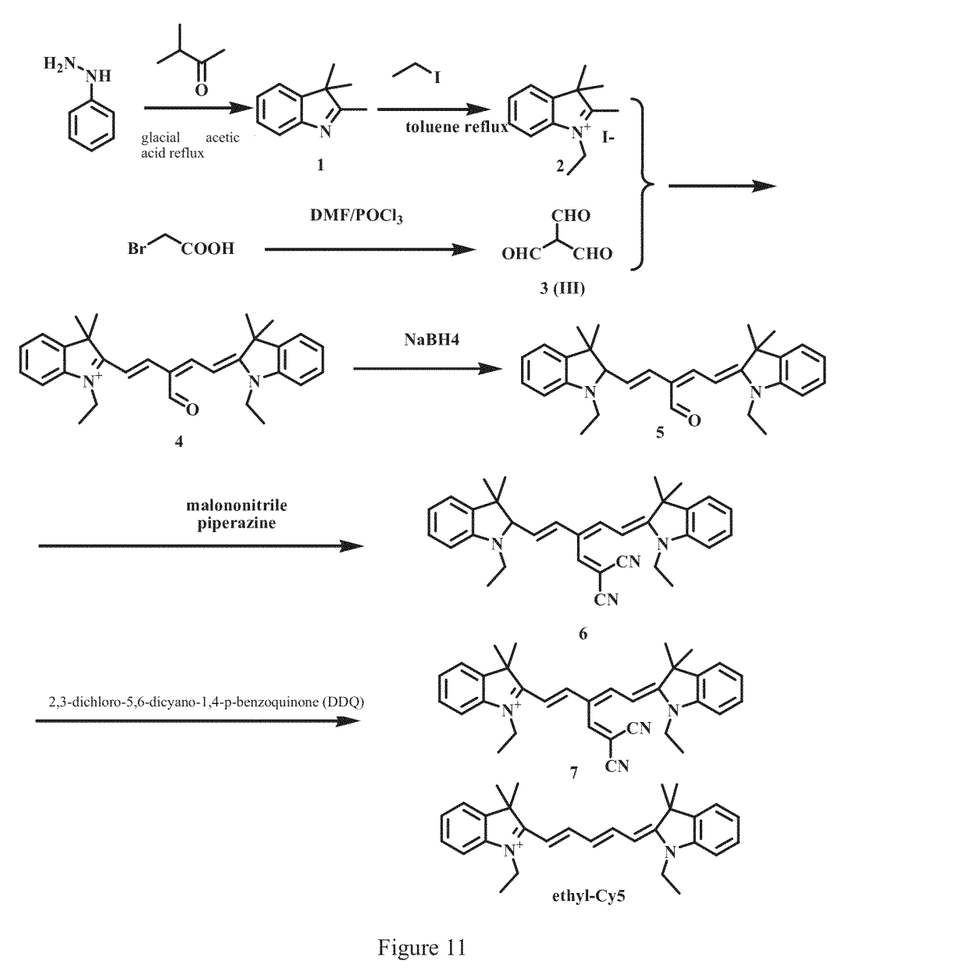
FIG. 11. Synthetic schemes of compounds 4 and 7.

Synthesis of 4 and 7
Synthetic schemes of 4 and 7 were shown in FIG. 11.

(1) Synthesis of 2,3,3-trimethyl-3H-indoline (the compound 1) according to Fisher indole synthesis method Phenylhydrazine 54 g (0.5 mol) was added into a 250 mL two-neck flask, and 3-methyl-2-butanone 43 g (0.5 mol) was added dropwise under stirring, the mixture was heated to 70-80° C. and reacted for 4 h, then the water layer was separated, and the separated water layer was extracted with diethyl ether. The organic phase was combined, dried with anhydrous $MgSO_4$ and filtered, and then solvent was removed under reduced pressure to obtain crude hydrazone 70 g (yield: 80%).

The obtained crude hydrazone 70 g (0.4 mol) was added into 150 mL glacial acetic acid, the obtained mixture was reacted at 90° C. oil bath for 3 h and then cooled down to room temperature. The water layer of the reaction solution was neutralized to neutral with saturated $Na_2CO_3$ aqueous solution, the water phase and the organic phase were separated, and the water phase was extracted with diethyl ether. The extracted liquid and the organic phase were combined, dried with anhydrous $Na_2SO_4$ and filtered, diethyl ether was removed by distillation, and then distillation was performed under reduced pressure to collect the fraction during 130-140° C. (0.08-0.09 Mp) as light yellow oil 52 g (yield: 82%).

(2) Synthesis of N-ethyl-2,3,3-trimethyl-3H-indolenium iodide quaternary ammonium salt (the c 2,3,3-trimethyl-3H-indoline 3.2 g (20 mmol) and iodoethane 4.7 g were mixed in a 100 mL round bottom flask, about 30 mL of toluene was added, and then the mixture was fluxed for 7 h under nitrogen atmosphere. The reaction solution was cooled down to room temperature, the solid was filtered and washed with diethyl ether to obtain pink solid quaternary ammonium salt 5.4 g (yield: 86%).

(3) Synthesis of 2-formyl-1,3-malondialdehyde (the compound 3)

In ice bath, $POCl_3$ (13.8 mL, 147 mmol) was added dropwise to DMF (40 mL, 518 mmol) over a period of 1 h by controlling the addition speed to keep the temperature during the addition not higher than 5° C. Color of the solution turned to orange at the end of the addition from green at the beginning of the addition. Then the ice bath was removed and the dense mixture was stirred at room temperature for another 1 h. Bromoacetic acid (7.15 g, 51 mmol) was added in batches, and the mixture was reacted for 24 h at 70° C. The brownish reaction liquid was decomposed with water of about 200 mL and then neutralized to about pH 8 with $Na_2CO_3$ carefully. Absolute ethanol of about 2 L was added and the inorganic salts were filtered off. The organic filtrate was dried slowly with air flow to obtain a pale yellowish residue, which was further neutralized with $H_2SO_4$ (50%, 10 mL), extracted with $CHCl_3$ (3×200 mL) and dried with anhydrous $MgSO_4$. Via sublimation step, a pure yellowish crystal 1.9 g was obtained (yield: 37%).

(4) Synthesis of 1,5-di(1-N-ethyl-3,3-dimethyl-2,3-H-lindoline)-3-formyl-1,3,5-pentatriene chloride quaternary ammonium salt cyanine dye (4)

1-ethyl-2,3,3-trimethyl-3H-indolenium iodide (1.3 g, 4 mmol) and triformylmethane (3) (0.2 g, 2 mmol) were added into a 50 mL round bottom flask, and then absolute ethanol 20 mL and several drops of pyridine were added. The solution was refluxed under nitrogen atmosphere for 1 h to turn to deep blue color, and cooled down to room temperature. The solvent was evaporated under reduced pressure. The product was washed with water, extracted with dichloromethane (3×20 mL) and dried with anhydrous $Na_2SO_4$. The solvent was removed by rotary evaporation. The residue was purified by silica gel chromatography using anhydrous methanol/dichloromethane (1/400, v/v) as an eluting solvent. A blue fraction was collected to obtain the final product 0.45 g, yield: about 51%. NMR and MS data of the product are shown below.

$^1$H-NMR (400 MHz, CDCl$_3$): 1.56 (t, 6H, CH$_3$, J=7.2 Hz), 1.86 (s, 6H, CH$_3$), 4.51 (q, 4H, CH$_2$, J=7.2 Hz), 7.22 (bp, 2H, CH), 7.33 (d, 2H, ArH, J=8.4 Hz), 7.38 (t, 2H, ArH, J=7.6 Hz), 7.46 (d, 2H, ArH, J=7.6 Hz), 7.49 (t, 2H, ArH, J=8.0 Hz), 8.26 (d, 2H, CH, J=14.4 Hz), 9.76 (s, 1H, CH,)

$^{13}$C-NMR (100 MHz, CDCl$_3$): 12.86, 28.39, 41.83, 50.93, 102.38, 112.14, 120.32, 122.83, 127.09, 129.18, 141.33, 142.25, 177.85, 189.74

HRMS-ESI: m/z calcd M$^+$ for C$_{30}$H$_{35}$N2O$^+$, 439.2749. found, 439.2764

(5) Synthesis of reduced product of 1,5-di(1-N-ethyl-3,3-dimethyl-2,3-H-lindoline)-3-formyl-1,3,5-pentatriene chloride quaternary ammonium salt cyanine dye (5)

1,5-bis(1-N-ethyl-3,3-dimethyl-2,3-H-lindoline)-3-formyl-1,3,5-pentatriene chloride quaternary ammonium salt cyanine dye (4) 0.566 g (1 mmol) was dissolved in 15 mL methanol to obtain a deep blue solution, and then NaBH$_4$ (10 mg, 0.25 mmol) was added. The solution was stirred at room temperature until turning to yellowish color. The solvent was removed under reduced pressure. The residue was simply purified by silica gel column chromatography using dichloromethane as an eluting solvent to obtain a light yellow product of about 0.41 g, yield: 93.2%. NMR data are shown below.

$^1$H NMR (400 MHz, CDCl$_3$): 1.10 (t, 3H, CH$_3$, J=6.4 Hz), 1.14 (s, 3H, CH$_3$), 1.27 (t, 3H, CH$_3$, J=6.4 Hz), 1.34 (s, 3H, CH$_3$), 1.68 (s, 6H, CH$_3$), 3.17 (q, 1H, CH$_2$, J=6.8 Hz), 3.33 (q, 1H, CH$_2$, J=6.8 Hz), 3.75 (q, 2H, CH$_2$, J=6.8 Hz), 5.99 (d, 1H, CH, J=12.8 Hz), 6.43 (d, 1H, ArH, J=8.4 Hz), 6.49 (d, 1H, ArH, J=7.6 Hz), 6.57 (d, 1H, CH, J=16.0 Hz), 6.68 (t, 1H, ArH, J=7.2 Hz), 6.78 (d, 1H, ArH, J=7.6 Hz), 7.01 (t, 2H, ArH, J=6.8 Hz), 7.08 (t, 1H, ArH, J=7.2 Hz), 7.24 (t, 2H, ArH, J=7.2 Hz), 7.49 (d, 1H, CH, J=13.2 Hz), 9.41 (s, 1H, CHO)

(6) Synthesis of reduced product of 1,5-di(1-N-ethyl-3,3-dimethyl-2,3-H-lindoline)-3-(2,2-dicyanovinyl)-1,3,5-pentatriene chloride quaternary ammonium salt cyanine dye (6)

The intermediate (5) (1.33 g, 3 mmol), malononitrile (0.66 g, 10 mmol) and anhydrous piperazine (0.86 g, 10 mmol) were dissolved in 30 mL anhydrous methanol, and stirred at room temperature overnight under nitrogen atmosphere. The reaction solution turned to pink color. The solvent was removed under reduced pressure. The residue was purified by silica gel column chromatography using dichloromethane as an eluting solvent to obtain a metallic luster powder 1.3 g, yield: 89%. NMR data are shown below.

$^1$H NMR (400 MHz, CDCl$_3$): 1.12 (t, 3H, CH$_3$, J=8.0 Hz), 1.29 (t, 3H, CH$_3$, J=8.0 Hz), 1.4 (s, 6H, CH$_3$), 1.67 (s, 6H, CH$_3$), 3.3 (q, 4H, CH$_2$, J=8.0 Hz), 5.86 (bp, 1H, CH), 5.95 (d, 1H, CH, J=12.0 Hz), 6.52 (bp, 1H, CH), 6.70 (bp, 2H, ArH), 6.89 (d, 1H, ArH, J=8.0 Hz), 7.02 (t, 1H, ArH, J=8.0 Hz), 7.11 (t, 2H, ArH, J=8.0 Hz), 7.19 (s, 1H, CH), 7.30 (t, 2H, ArH, J=8.0 Hz), 7.71 (d, 1H, CH, J=12.0 Hz)

(7) Synthesis of 1,5-di(1-N-ethyl-3,3-dimethyl-2,3-H—lindoline)-3-(2,2-dicyanovinyl)-1,3,5-pentatriene chloride quaternary ammonium salt cyanine dye (7)

6 0.98 g (2 mmol) was dissolved in 20 mL anhydrous dichloromethane, and then 2, 3-dichloro-5,6-dicyano-1,4-p-benzoquinone (DDQ, 0.452 g, 2 mmol) was added. The solution was stirred at room temperature until the reaction was completed (TLC tracking inspection), the solution changed into deep blue color from pink color. The solvent was removed under reduced pressure. The residue was washed with saturated saline, extracted with dichloromethane, and dried with anhydrous Na$_2$SO$_4$. Then the residue obtained by removing the solvent under reduced pressure was purified by silica gel column chromatography (using dichloromethane/methanol of 99:1 (v/v) as an eluting solvent) to obtain a metallic luster powder 0.56 g, yield: 53.6%. NMR and MS data are shown below.

$^1$H NMR (400 MHz, CDCl$_3$): 1.54 (t, 6H, CH$_3$, J=6 Hz), 1.83 (s, 12H, CH$_3$), 4.59 (q, 4H, CH$_2$, J=6.0 Hz), 6.66 (d, 2H, CH, J=14.8 Hz), 7.34 (d, 2H, ArH, J=8.0 Hz), 7.39 (d, 2H, ArH, J=7.2 Hz), 7.46 (t, 4H, ArH, J=7.2 Hz), 8.03 (s, 1H, CH), 8.53 (d, 2H, CH, J=14.8 Hz);

$^{13}$C-NMR (100 MHz, CDCl$_3$): 12.95, 27.55, 41.26, 51.03, 102.92, 112.26, 115.45, 116.16, 116.96, 122.63, 127.34, 129.01, 140.96, 142.39, 148.81, 154.18, 177.37; HRMS-ESI: m/z calcd M$^+$ for C$_{33}$H$_{35}$N$_4$$^+$, 487.2862. found, 487.2866

Example 2

Analysis of Spectral Properties of 4 and 7

Firstly, stock solutions of 4 and 7 in DMSO were prepared respectively. Then sample solutions of 1 μM were prepared by diluting the mother liquors with corresponding chromatography grade solvent. UV absorption and fluorescence emission spectra of the sample solutions in different solvents were measured at room temperature, the results were shown in FIGS. 1A and 1B, respectively. In the meanwhile, spectral properties of 4, 7 and ethyl-Cy5 were also investigated; the results were shown in table 1.

Figure 1:
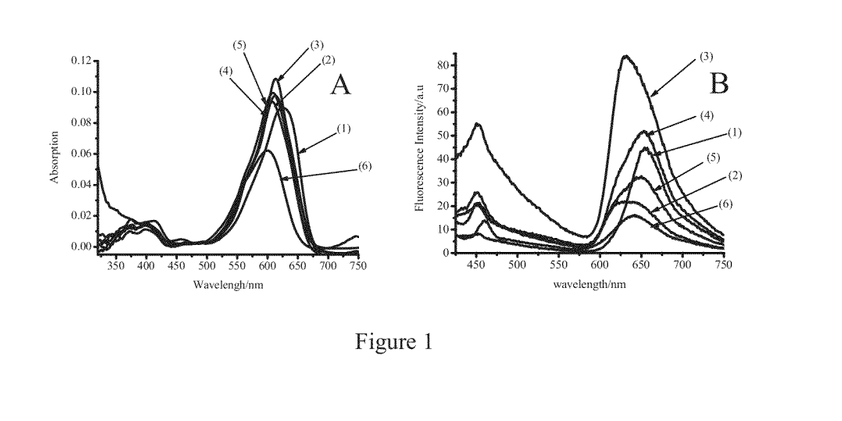
FIG. 1. Absorption and emission spectra of the compound 4 in different solvents ($\lambda_{ex}$=600 and 400 nm, 1 μM) and fluorescence increase fold.

From the results, it can be seen that, compared with the traditional pentamethine cyanine fluorescent dye (ethyl-Cy5), both 4 and 7 as fluorescence probe have two groups of absorption peaks and emission peaks (400 and 610 nm, 456 and 650 nm for 4; 510 and 655 nm, 565 and 668 nm for 7). In ethanol, fluorescence quantum yields of 4, 7 and ethyl-Cy5 are 0.0108, 0.0048 and 0.27, respectively, fluorescence quantum yields of the former two dyes are obviously lower than that of traditional Cy5 (results are shown in Table 1), and fluorescence quantum yields of the two dyes change little with the increase of solvent polarity, namely, the dyes are little influenced by solvent polarity and insensitive to solvent. Structurally, it is equivalent to overlapping of two fluorescent dyes, namely, absorption and emission from two groups of longer wavelengths (610, 650 nm and 655, 668 nm) respond to normal absorption peak and emission peak of the cyanine dye, and two groups of shorter wavelength peaks (400, 460 nm and 510, 565 nm) originate from the introduced conjugation group at central position (aldehyde group or malononitrile vinyl group) which generated a group of new electronic transition state. Namely, the transition of shorter conjugation chain fluorophore occurs and intramolecular electric charge redistribution between two fluorescent dyes in excited state happens, so the dyes emit longer wavelength fluorescence by the excitation of shorter wavelength (results are shown in FIG. 1 and Table 1) to obtain a large pseudo-Stokes Shift (254 and 158 nm in ethanol, respectively). The dyes are very sensitive to environmental viscosity, and their fluorescence intensities are greatly enhanced with the increase of solution viscosity, but UV absorption spectra influence little by solution viscosity.

TABLE 1

Comparison of spectral properties of 4, 7 and traditional ethyl-Cy5

| compound | solvent | $\lambda_{abs1}{}^a$ | $\lambda_{abs2}{}^a$ | $\lambda_{em1}{}^a$ | $\lambda_{em2}{}^a$ | $\Delta\lambda_1{}^b$ | $\Delta\lambda_2{}^b$ | $\Delta\lambda_3{}^b$ | $\epsilon_1{}^c$ | $\epsilon_2{}^c$ | $\Phi_1{}^d$ | $\Phi_2{}^d$ |
|---|---|---|---|---|---|---|---|---|---|---|---|---|
| 4 | dichloromethane | 399 | 625 | 454 | 654 | 55 | 29 | 255 | 1.60 | 8.97 | 0.0060 | 0.0231 |
|  | acetonitrile | 397 | 607 | 451 | 626 | 54 | 19 | 229 | 1.12 | 9.35 | 0.0062 | 0.0071 |
|  | DMSO | 400 | 613 | 451 | 630 | 51 | 17 | 230 | 1.5 | 10.85 | 0.0158 | 0.0224 |
|  | ethanol | 399 | 613 | 451 | 653 | 52 | 40 | 254 | 1.38 | 9.75 | 0.0050 | 0.0108 |
|  | methanol | 400 | 608 | 451 | 650 | 51 | 42 | 250 | 1.45 | 9.93 | 0.0050 | 0.0079 |
|  | water | 413 | 600 | 460 | 643 | 47 | 43 | 230 | 1.68 | 6.21 | 0.0023 | 0.0032 |
| 7 | dichloromethane | 512 | 656 | 568 | 672 | 56 | 16 | 160 | 4.97 | 11.35 | 0.0016 | 0.006 |
|  | acetonitrile | 513 | 635 | 561 | 661 | 48 | 25 | 148 | 5.94 | 11.20 | 0.0017 | 0.0019 |
|  | DMSO | 522 | 639 | 569 | 670 | 47 | 31 | 148 | 4.50 | 11.82 | 0.0057 | 0.0113 |
|  | ethanol | 510 | 641 | 566 | 668 | 56 | 27 | 158 | 5.31 | 12.56 | 0.0022 | 0.0048 |
|  | methanol | 509 | 636 | 568 | 665 | 59 | 25 | 156 | 4.90 | 12.20 | 0.0022 | 0.0031 |
|  | water | 520 | 627 | 570 | 655 | 50 | 28 | 135 | 3.10 | 5.24 | 0.0006 | 0.0028 |
| ethyl-Cy5 | dichloromethane |  | 661 |  | 671 |  | 6 |  |  | 30.6 |  | 0.29 |
|  | THF |  | 653 |  | 662 |  | 9 |  |  | 22.7 |  | 0.37 |
|  | DMSO |  | 655 |  | 668 |  | 13 |  |  | 27.2 |  | 0.33 |
|  | ethanol |  | 652 |  | 663 |  | 11 |  |  | 30.2 |  | 0.27 |
|  | methanol |  | 649 |  | 659 |  | 10 |  |  | 25.9 |  | 0.22 |
|  | water |  | 648 |  | 656 |  | 8 |  |  | 22.7 |  | 0.13 |

[a] maximum absorption and emission wavelength (nm) of dyes in different solvents;
[b] Stokes Shift (nm), $\Delta\lambda_1 = \lambda_{em1} - \lambda_{abs1}$, $\Delta\lambda_2 = \lambda_{em2} - \lambda_{abs2}$, $\Delta\lambda_3 = \lambda_{em2} - \lambda_{abs1}$;
[c] molar extinction coefficient ($\times 10^4$ L/cm · mol);
[d] Rhodamine B in ethanol (fluorescence quantum yield is 0.97) was used as reference stoodard, the first absorption peak of dye was chosen as excitation wavelength.

Example 3

Viscosity Experiments of Compounds 4 and 7

Firstly, DMSO solutions of 4 and 7 having a concentration of $1.0 \times 10^{-3}$ M were prepared, respectively. The stock solution of 10 L was added into 10 mL glycerol-ethanol mixture, and ultrasonicated to remove bubbles. The solution stayed for 1 hour, and then absorption and emission spectra therefore were measured by using UV-visible spectrophotometer and fluorescence spectrophotometer, and fluorescence lifetime of solution with different viscosity was detected as well. UV-visible spectrophotometer, model: Hp8453; fluorescence spectrophotometer model: FP-6500; Fluorescence lifetime equipment: Horiba Jobin Yvon Fluoromax-4-p.

Glycerol-ethanol mixture was a mixture of glycerol and ethanol, $V_{glycerol}:V_{ethanol}$ were 1:9, 2:8, 3:7, 4:6, 5:5, 6:4, 7:3, 8:2 and 9:1.

Figure 2:
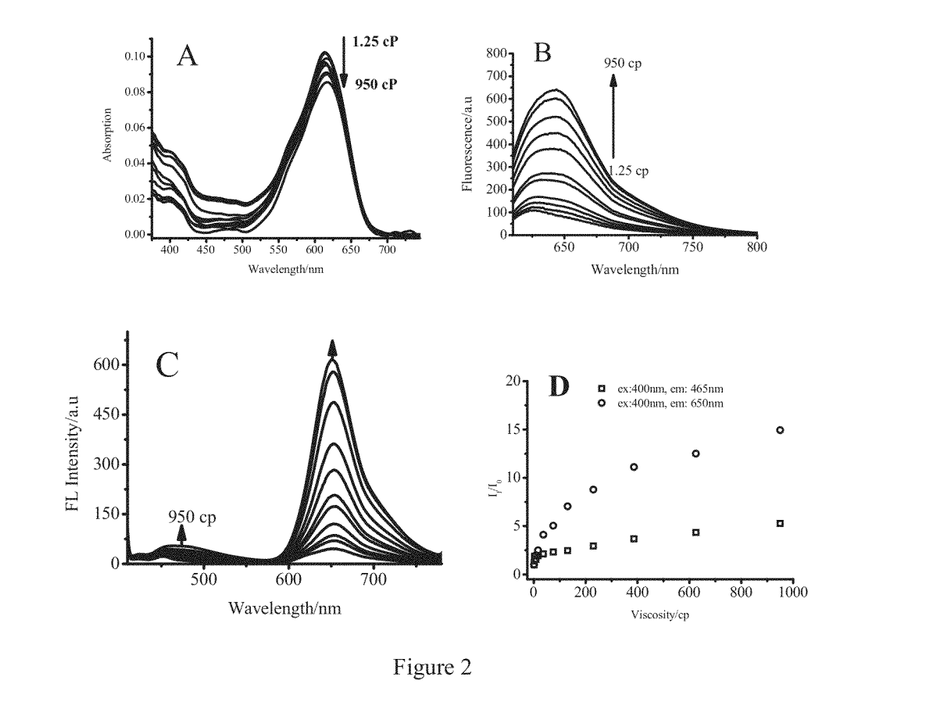
FIG. 2A. Changes of absorption spectra of the compound 4 (1 μM) in the solutions with different viscosity ($\lambda_{ex}$=410 and 600 nm) and fluorescence increase fold at each emission peak.
FIG. 2B. Changes of emission spectra of the compound 4 (1 μM) in the solutions with different viscosity ($\lambda_{ex}$=600 nm).
FIG. 2C. Changes of emission spectra of the compound 4 (1 μM) in the solutions with different viscosity ($\lambda_{ex}$=410 nm).
FIG. 2D. Fluorescence increase fold at emission peaks of 460 nm and 650 nm when exciting the compound 4 (1 μM) at 410 nm.

After the solution stayed for a period of time at some temperature for bubbles disappearing, UV-visible absorption spectrum (as shown in FIG. 2A) and fluorescence emission spectrum (as shown in FIGS. 2B and 2C) of the compound in the solvent with different volume ratio of glycerol and ethanol were measured by using UV-visible spectrophotometer and fluorescence spectrophotometer. FIG. 1 demonstrated that absorption and emission of the dye changed little with the variation of solvents with low viscosity, and UV absorption of the dye also changed little. On the other hand, fluorescence of the dye was greatly increased when viscosity was gradually enhanced, and the fluorescence intensity was increased as large as by 15 and 4 folds at 650 and 456 nm when excited at 600 and 400 nm (as shown in FIG. 2D), respectively. The logarithm of fluorescence intensity kept good linear relationship with that of viscosity (as shown in FIG. 3A), well fitting for Förster-Hoffmann equation, which can be used to detect viscosity of homogeneous phase solution. Moreover, the logarithm of ratio value of fluorescence intensities at 650 nm and 456 nm also kept good linear relationship with that of viscosity (as shown in FIG. 3B), which can be employed to detect viscosity of biological environment (such as inside cells).

Compared with spectral properties of 4 and ethyl-Cy5, for 7, maximum absorption and emission wavelengths red shifted, two groups of absorption and emission peaks existed, and its fluorescent quantum yield kept very low in the low-viscosity solvents with different polarity. As shown in Table 1, fluorescence quantum yields of the compound 7 in dichloromethane with weaker polarity were 0.0016 and 0.006, and fluorescence quantum yields in water with strong polarity at two emission peaks were 0.0006 and 0.0028, respectively. Namely, fluorescence quantum yield of the dye changed little when polarity changed much but viscosity changed little, demonstrating that the dye was insensitive to solvent polarity.

Figure 4:
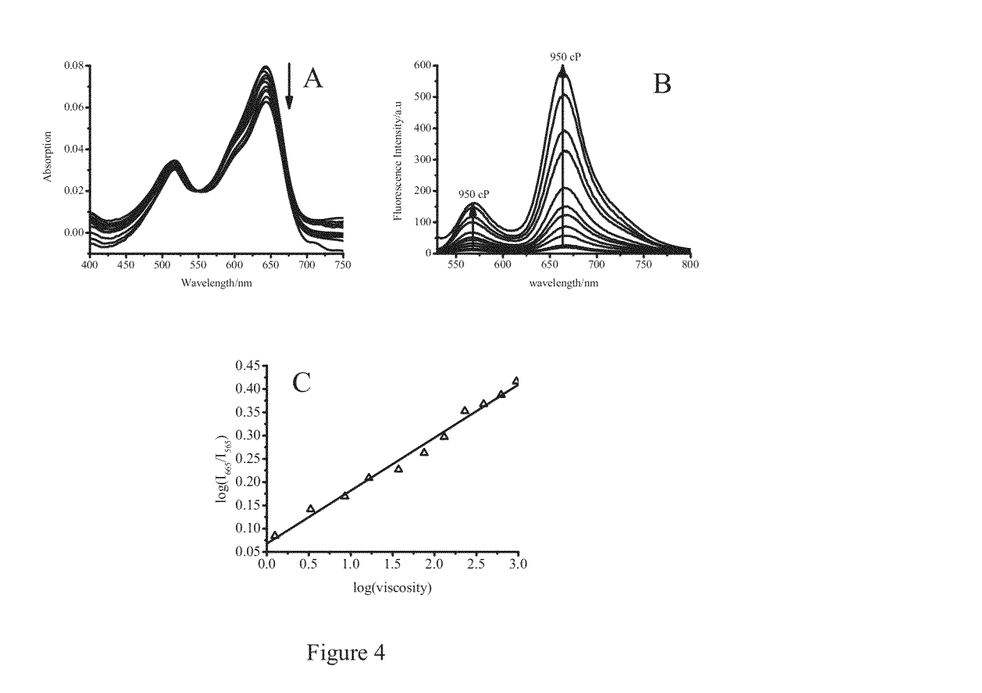
FIG. 4. Changes of UV absorption and fluorescence emission spectra of the compound 7 in solutions with different viscosity, and linear relationship between the logarithm of ratio value of fluorescence intensity and the logarithm of solution viscosity.

Fluorescence increase of 7 in the solutions with different viscosity was very similar to that of 4. As shown in FIG. 4, UV absorption of 7 kept constant with the variation of solution viscosity (FIG. 4A), but dramatic fluorescence increase can be observed when viscosity was increased (FIG. 4B), and moreover, the fluorescence at 665 nm was increased much more than that at 565 nm. It fit well for Förster-Hoffmann equation between the logarithm of ratio value of fluorescence intensities at two emission peaks and the logarithm of solution viscosity (FIG. 4C), and can be used to detect solution viscosity. In another aspect, fluorescence lifetime at 665 nm for 7 was also obviously elongated with the increase of solution viscosity (FIG. 5A), and the relationship between fluorescence lifetime and solution viscosity also fit well for Förster-Hoffmann equation (FIG. 5B). Namely, 7 can also be employed to evaluate solution viscosity by dual detection models as 4.

The fluorescence quantum yields of 4 and 7 were rather low, demonstrating low background fluorescence. As shown in Table 1, the compound 4 and 7 were insensitive to solvent polarity. The fluorescence intensities of 4 and 7 were quite sensitive to solvent viscosity. The fluorescence intensity of the probe was rapidly increased when the viscosity was enhanced, when excited at longer wavelength, the fluorescence intensity of the probe at longer wavelength was increased correspondingly, and when excited at shorter wavelength, both of the fluorescence intensities at shorter and longer wavelengths were increased correspondingly to 15 and 4 folds, respectively.

The logarithm of fluorescence intensity and that of viscosity have good linear relationship and fit well for Förster-Hoffmann equation (equation 1):

$$\log I_f = C + x \log \eta \quad \text{(equation 1)}$$

wherein, $I_f$ means fluorescence intensity of the dye; C means temperature constant; x means constant of the dye; and $\eta$ means solvent viscosity.

Figure 3:
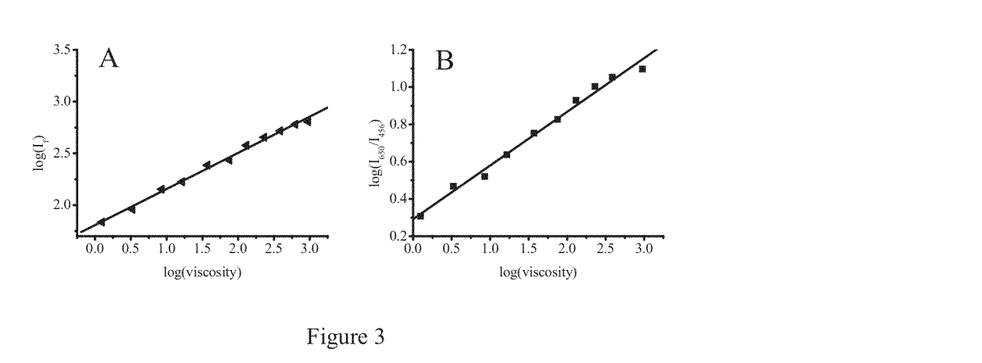
FIG. 3A. Linear relationship between the log($I_{650}$) of 4 vs. log(viscosity).
FIG. 3B. Linear relationship between the logarithm of log($I_{650}/I_{465}$) of the compound 4 vs. log(viscosity).

There were two groups of emission peaks, and the increased folds in fluorescence intensities at each group of emission peaks were different with the increase of viscosity. The ratio of fluorescence intensities at two groups of emission peaks was calculated, and it was found that the logarithm of the ratio and that of viscosity had good linear relationship and fit well for Förster-Hoffmann equation as well. Therefore, 4 and 7 can be used as ratiometric probes (results are shown in FIGS. 3 and 4).

Inhomogeneous concentration of the dye in solution may affect fluorescence intensity to produce error and affect detection accuracy. The ratiometric method is satisfactory in avoiding the error caused by the above problem. Fluorescence lifetime of the fluorescent dye is also not affected by inhomogeneous concentration of the dye and the similar detection result can be achieved. According to the work of Suhling and his coworkers, the fluorescence lifetime method can be employed to detect environmental viscosity because of the different fluorescence lifetime of the dye in the different environmental viscosity.

Figure 5:
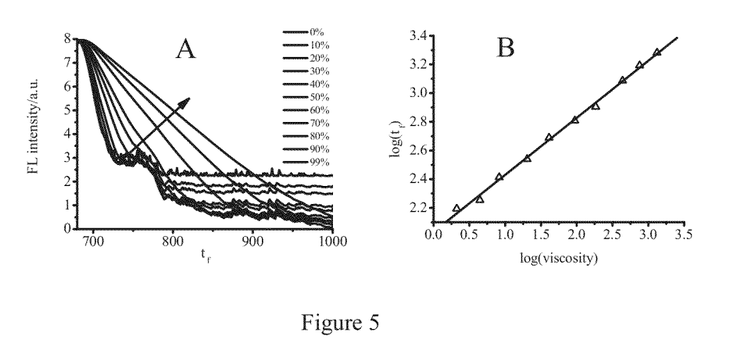
FIG. 5. Changes of fluorescence lifetime of 7 in the solutions with different viscosity.
Figure 7:
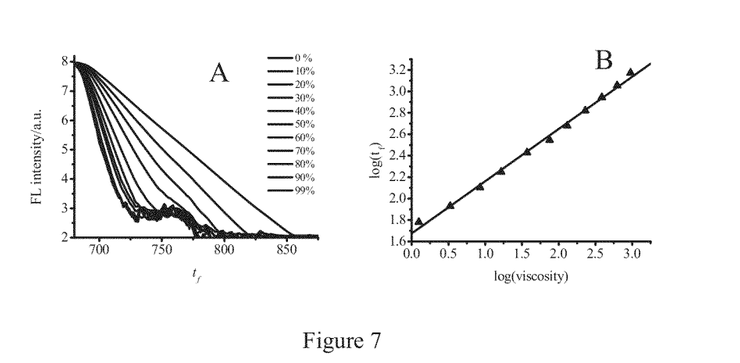
FIG. 7. Fluorescence lifetime plot of 4 in glycerol-ethanol mixtures with different viscosity, and linear relationship of log(τ) and log(viscosity), fluorescence lifetime equipment version: Horiba Jobin Yvon Fluoromax-4-p, excited at 376 nm.

As shown in FIGS. 5 and 7, the increase in fluorescence lifetime of the dye 4 is not evident in the solution with low viscosity, but the great increase in fluorescence lifetime of the dye can be detected once the solution becomes viscous enough, and the fluorescence lifetime is increased from lower than 50 ps in pure ethanol to 1450 ps in 99% glycerol solution. The logarithm of the fluorescence lifetime and that of the solution viscosity have good linear relationship and fit well for Förster-Hoffmann equation. The similar changes in fluorescence lifetime can be observed for 7 and 4, so both dyes can be used to detect the viscosity of solution or biological environment by fluorescence lifetime method.

Example 4

Cell Experiments Using 4 and 7

Observation of living cell (MCF-7 cell) stained by the compound under laser confocal scanning microscopy The compounds 4 and 7 (12 μL, 5 μM) in PBS buffer were added into a 6-well plate with incubated MCF-7 cells, and then the plate was incubated for 30 minutes in a cell incubator of 37° C. and 5% $CO_2$. The plate was rinsed with PBS for 5 min×3 times, fresh culture medium was added thereto, and the cells were observed under laser confocal scanning microscopy (Leica, TCS-SP2, Germany). Typical region was selected, the traditional Cy5 was excited at 633 nm and 7 was excited at 514 nm, the cells were observed under oil immersion lens (1000×) for three times.

Figure 6:
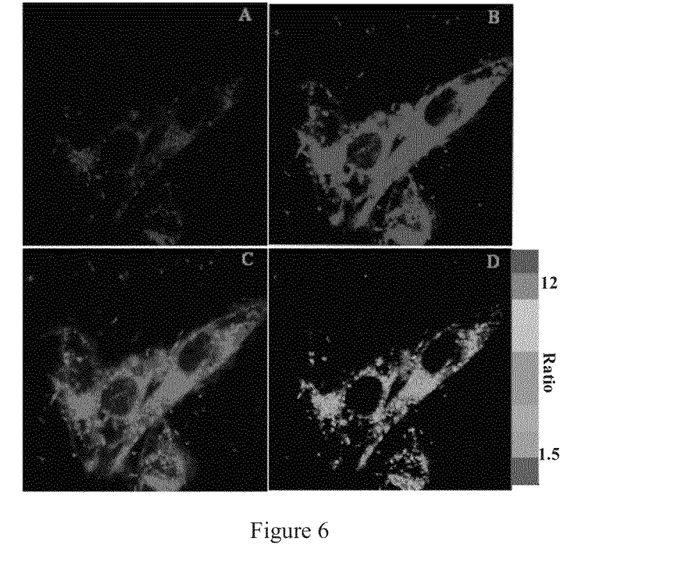
FIG. 6. Fluorescence imaging of 4 (5 μM) in MCF-7 cells, Leica laser confocal fluorescence microscopy×100 objective lens, excited at 800 nm.
Figure 9:
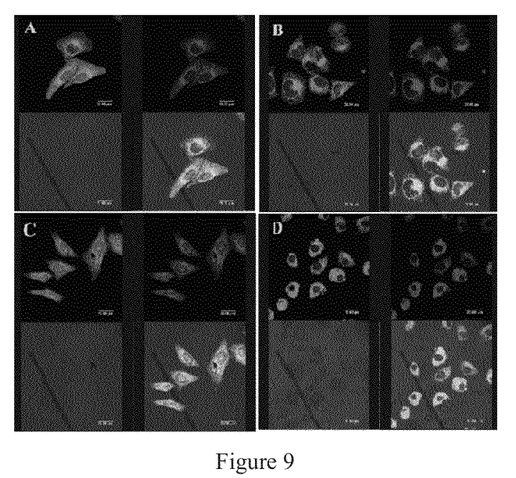
FIG. 9. Fluorescence image of 7 in MCF-7 cells, $\lambda_{ex}$=514 nm, Leica TCS-SP2 laser confocal microscopy, 100× objective lens.

FIGS. 6 and 9 are fluorescence microscopy image of living cell (MCF-7 cell) stained by 4 and 7, respectively. From these figures, the large fluorescence difference in MCF-7 cells stained by the traditional Cy5 and 4 can be observed. Laser confocal scanning microscopy TCS-SP2 was used, and excitation channels were Cy5 (633 nm), green light (543 nm), cyan light (488 nm) and blue light (388 nm).

Direct Staining by the Dye

MCF-7 cells and Hela cells were inoculated on a 6-well plate and cultured for 24 hours at 37° C. and 5% $CO_2$. Then, the dye was added in a final concentration of 5 μM, and the plate was incubated at 37° C. for 30 min. The culture medium was moved off, and the plate was rinsed with PBS for two times. Fresh culture medium 1200 μL was added and the fluorescence was excited.

$H_2O_2$ Damaging

MCF-7 cells and Hela cells were inoculated on a 6-well plate and cultured for 24 hours at 37° C. and 5% $CO_2$. Then, $H_2O_2$ 133.3 L was added in a final concentration of 1 mM/L, and the plate was incubated at 37° C. for 2 hours. The culture medium was moved off, and the plate was rinsed with PBS for two times. Fresh culture medium 1200 μL was added and then the dye was added in a final concentration of 5 μM, the plate was incubated at 37° C. for 30 min. The culture medium was moved off, and the plate was rinsed with PBS for two times. Fresh culture medium 1200 μL was added and the fluorescence was excited.

Ethanol Fixing

MCF-7 cells and Hela cells were inoculated on a 6-well plate and cultured for 24 hours at 37° C. and 5% $CO_2$. The culture medium was moved off, and the plate was rinsed with PBS for two times. Appropriate amount of 70% ethanol was added and then the plate was incubated at 37° C. for 30 min. Ethanol for fixing was moved off, and the plate was rinsed with PBS for two times. PBS 1200 μL was added and then the dye was added in a final concentration of 5 μM, the plate was incubated at 37° C. for 30 min and the fluorescence was excited.

The dye disclosed in the present invention is live cell membrane permeable. After entering into the cell, the probe locates in the different regions inside cell, and shows different fluorescence increase, as demonstrated in FIG. 6 which is the imaging figure of the compound 4 in MCF-7 cells. The dye has two emission wavelengths located at 460 nm and 650 nm, respectively, so dual channel detection was used. The short wavelength channel was blue channel (460±20) nm (FIG. 6A) and the long wavelength channel was red channel (650±20) nm (FIG. 6B). The merged image by blue channel and red channel was pink color (FIG. 6C). The ratio of fluorescence intensities at two channels was calculated to obtain the ratiometric image of the compound 4 in MCF-7 cells (FIG. 6D). According to the figures, different viscosity distribution inside cells can be clearly found, so the method can be used to map different viscosity distribution inside cells.

Figure 8:
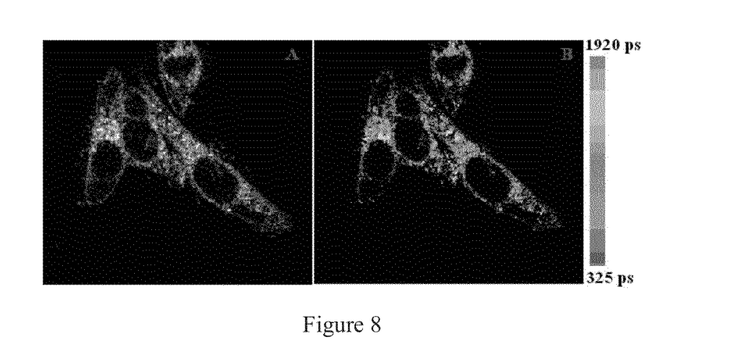
FIG. 8. Fluorescence intensity imaging and fluorescence lifetime imaging of the compound 4 (5 μM) in MCF-7 cells.

According to the work by Suhling and his coworkers, the logarithm of fluorescence lifetime of the probe kept linear relationship with that of viscosity, and well fit for Förster-Hoffmann equation. The compound 4 can be employed to detect intracellular viscosity distribution by fluorescence lifetime imaging. As shown in FIG. 8, distribution of 4 inside MCF-7 cells may be observed according to fluorescence intensity, and the dye exists throughout the cell. Different distribution of fluorescence lifetime of 4 in variable regions inside cells indicated different viscosity distribution inside cells. From fluorescence lifetime image (FIG. 8), it can be seen that the difference of fluorescence lifetime of the compound 4 in different environment reflects the difference of viscosity in different position of cells, so fluorescence lifetime imaging for 4 inside cells can clearly show viscosity distribution inside cells.

According to the above results, the result obtained in ratiometric imaging and the result obtained in fluorescence lifetime imaging are consistent, and the bigger ratio corresponds to the longer fluorescence lifetime, which proves accuracy of ratiometric imaging and fluorescence lifetime imaging.

Ratiometric imaging detection and fluorescence lifetime imaging detection for 4 in cells have been mainly illustrated.

The same detection results can be obtained for 7 by using dual model to image intracellular viscosity distribution.

Figure 10:
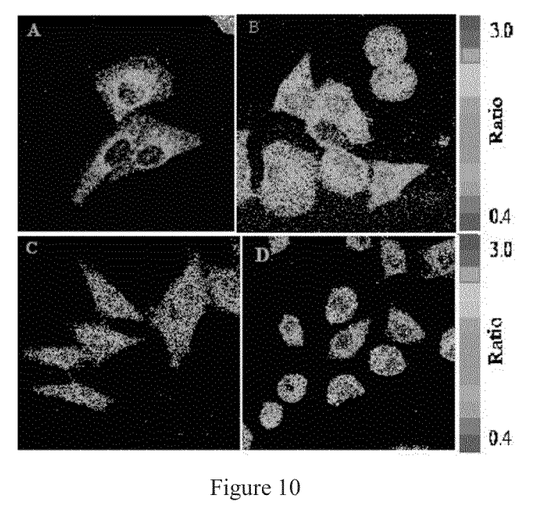
FIG. 10. Ratiometric fluorescence imaging of 7 in MCF-7 cells, $\lambda_{ex}$=514, Leica TCS-SP2 laser confocal microscopy, 100× objective lens.

As demonstrated in FIG. 9 and FIG. 10, there are two emission wavelengths located at 565 nm and 665 nm for 7. Dual channel detection, namely green channel (565±20) nm and red channel (665±20) nm, was employed. Four groups of cell experiments had been done: (1) cells were incubated with 7 and then observed under laser confocal microscopy; (2) after incubation with the dye, cells were incubated with hydrogen peroxide (1 mM) for half an hour to induce cell apoptosis; (3) cells were fixed by incubation with ethanol; and (4) after incubation with 7, cells stood for 4 hours at room temperature, results are shown in FIG. 9. From ratiometric images obtained by Image Pro-plus software, it can be found that: (1) viscosity inside normal live cells was low, the dye showed blue color in most of regions of cells, and ratio value was small; (2) after cells were treated by hydrogen peroxide and cell apoptosis was induced, the color inside cells changed evidently, and ratio value was increased which demonstrated viscosity increase inside cells correspondingly; (3) when cells were fixed, cells were surely dead, the similar results were obtained as those of (2); (4) cells were dying, ratio value of the probe was between (1) and (2), namely, an intermediate state. In conclusion, the compound 7 can be used to detect intracellular viscosity change and to investigate cell apoptosis process.

The invention claimed is:

1. A pentamethine cyanine fluorescent dye of formula I:

I wherein
X is CHO or CHCR$_3$R$_4$;
R$_1$ and R$_2$ are independently selected from the group consisting of (CH$_2$)$_n$R$_7$, (CH$_2$)$_m$OR$_8$, (CHR$_9$CH$_2$O)$_p$R$_8$ and CH$_2$C$_6$H$_4$R$_7$;
R$_3$ and R$_4$ are independently selected from the group consisting of CN, COOH and COOR$_{16}$;
R$_5$, R$_6$ and R$_7$ are independently selected from the group consisting of H, SO$_3$R$_{10}$ and COOR$_{11}$;
R$_8$ is H or C$_{1-18}$ alkyl;
R$_9$ is H or CH$_3$;
R$_{10}$ is N(R$_{12}$R$_{13}$R$_{14}$R$_{15}$);
R$_{11}$ is C$_{1-18}$ alkyl;
R$_{12}$, R$_{13}$, R$_{14}$, R$_{15}$ and R$_{16}$ are independently selected from the group consisting of H, C$_{1-18}$ alkyl, (CH$_2$)$_m$OR$_8$ and (CHR$_9$CH$_2$O)$_p$R$_8$;
Y− is halogen anion or OTs−; and
n, m and p are integers of 0-18.

2. The compound according to claim 1, wherein R$_3$ and R$_4$ are CN.

3. The compound according to claim 1, wherein R$_1$ and R$_2$ are independently selected from (CH$_2$)$_n$R$_7$.

4. The compound according to claim 1, wherein R$_5$ and R$_6$ are H.

5. The compound according to claim 2, wherein R$_1$ and R$_2$ are CH$_3$, R$_5$ and R$_6$ are H.

6. A synthesis method of the compound according to claim 1, comprising the following steps:

(1) 2,3,3-trimethyl-3H-indole with a substituent group of R$_5$ is reacted with R$_1$CH$_2$Z to obtain a quaternary ammonium salt II, wherein Z is halogen or OTs, Z− is halogen anion or OTs−, reaction temperature is 80-148° C., reaction time is 6-12 hours, reaction solvent is selected from the group consisting of toluene, ortho-dichlorobenzene, ethanol and acetonitrile, and molar ratio of the indole compound to R$_1$CH$_2$Z is 1:1-1:4;

II (2) 2-bromoacetic acid is reacted with POCl$_3$ and DMF to obtain an intermediate III with multi aldehyde groups, wherein molar ratio of 2-bromoacetic acid to POCl$_3$ is 1:4-1:6, and reaction temperature is 70±2° C.;

III (3) the quaternary ammonium salt II obtained in the step (1) and the intermediate III obtained in the step (2) are refluxed for 2-6 hours in ethanol solvent with pyridine as a catalyst to obtain a pentamethine cyanine fluorescent dye of formula IV with aldehyde group at central position, wherein when molar ratio of the intermediate III to the quaternary ammonium salt II is 1:3, the product is a symmetrical pentamethine cyanine fluorescent dye with aldehyde group at the central position, while when two kinds of the quaternary ammonium salts are used, and molar ratio of the intermediate III, the first quaternary ammonium salt and the second quaternary ammonium salt is 1:0.8-1:1-3, the product is an asymmetrical pentamethine cyanine fluorescent dye with aldehyde group at the central position;

IV

(4) the compound IV obtained in the step (3) is reacted with NaBH$_4$ in methanol to obtain a compound V;

(5) the compound V obtained in the step (4) is reacted with R$_3$CH$_2$R$_4$ under basic condition to obtain a compound VI, wherein reaction solvent is anhydrous methanol, reaction temperature is 25-40° C., and molar ratio of the compound V to R$_3$CH$_2$R$_4$ is 1:2-1:4;

(6) the compound VI obtained in the step (5) is oxidized and dehydrogenated to obtain a compound VII, wherein solvent is dichloromethane or chloroform, oxidation-dehydrogenation reagent is 2,3,5,6-tetrachloro-1,4-p-benzoquionone or 2,3-dichloro-5,6-dicyano-1,4-p-benzoquionone, and molar ratio of the compound V to the oxidation-dehydrogenation reagent is 1:0.5-1:1;

(7) ion exchange is performed between the compounds IV and VII with a sodium salt or a potassium salt containing Y− anion to obtain the compound of formula I.

7. A method for detecting fluid viscosity, comprising:
introducing a compound of claim 1 into a fluid;
measuring a fluorescence intensity or a fluorescence lifetime of the fluid obtained in step (1);
correlating a change in the fluorescence intensity or the fluorescence lifetime to a change in the fluid viscosity.

8. The compound according to claim 2, wherein R$_1$ and R$_2$ are independently selected from (CH$_2$)$_n$R$_7$.

9. The compound according to claim 2, wherein R$_5$ and R$_6$ are H.

10. The method of claim 7, wherein the fluid is an intracellular fluid.

* * * * *